United States Patent [19]
Ogita

[11] Patent Number: 4,693,704
[45] Date of Patent: Sep. 15, 1987

[54] CERVICAL CANAL CATHETER

[75] Inventor: Sachio Ogita, 9-19, Amamihigashi-6-chome, Matsubara-shi, Osaka-fu, Japan

[73] Assignees: Sumitomo Bakelite Company Limited, Toyko; Sachio Ogita, Osaka, both of Japan

[21] Appl. No.: 824,316

[22] PCT Filed: Oct. 12, 1983

[86] PCT No.: PCT/JP83/00340

§ 371 Date: Jun. 5, 1984

§ 102(e) Date: Jun. 5, 1984

[87] PCT Pub. No.: WO84/01514

PCT Pub. Date: Apr. 26, 1984

Related U.S. Application Data

[63] Continuation of Ser. No. 619,150, Jun. 5, 1984, abandoned.

[30] Foreign Application Priority Data

Oct. 12, 1982 [JP] Japan .................................. 57-17759

[51] Int. Cl.[4] .............................................. A61M 25/00
[52] U.S. Cl. ....................................... 604/55; 604/101
[58] Field of Search ...................... 604/101, 21, 53, 55, 604/96, 102, 103, 104

[56] References Cited

U.S. PATENT DOCUMENTS

| | | | |
|---|---|---|---|
| 550,238 | 11/1895 | Allen, Jr. | 604/102 |
| 2,175,726 | 10/1939 | Gebajer | 604/102 |
| 2,210,744 | 8/1940 | Winder | 604/101 |
| 2,642,874 | 6/1953 | Keeling | 604/102 |
| 2,693,191 | 11/1954 | Raiche | 604/101 |
| 2,930,377 | 3/1960 | Cowley | 604/103 |
| 2,936,760 | 5/1960 | Gants | 604/102 |
| 3,154,077 | 10/1964 | Cannon | 604/101 |
| 3,503,400 | 3/1970 | Osthagen et al. | 604/249 |
| 3,818,511 | 6/1974 | Goldberg et al. | 604/175 |
| 3,866,599 | 2/1975 | Johnson | 604/96 |
| 4,093,484 | 6/1978 | Harrison et al. | 604/96 |
| 4,100,923 | 7/1978 | Southern | 604/55 |
| 4,180,076 | 12/1979 | Betancourt | 604/101 |
| 4,256,102 | 3/1981 | Monaco | 604/175 |
| 4,351,342 | 9/1982 | Wilta . | |
| 4,430,076 | 2/1984 | Harris | 604/96 |
| 4,571,241 | 1/1986 | Christopher | 604/104 |

FOREIGN PATENT DOCUMENTS

| | | | |
|---|---|---|---|
| 2454589 | 11/1974 | Fed. Rep. of Germany . | |
| 2380032 | 2/1977 | France . | |
| 72860 | 5/1970 | German Democratic Rep. | 604/101 |

*Primary Examiner*—Stephen C. Pellegrino
*Attorney, Agent, or Firm*—Browdy and Neimark

[57] ABSTRACT

This invention relates to a cervical canal catheter devised inorder not only to prevent possible complications accompanying the premature rupture of membrane in a pregnant woman, but also to carry extraction after positively awaiting the fetal maturity. Said catheter is made of a soft rubber or resin, has a gourd-shaped balloon or two independent balloons at the tip, and is used for preventing the efflux of amniotic fluid and the concomitant onset of labor-pains by inserting the catheter into cervical canal, expanding the balloon or balloons, and attaching the catheter by a conventional surgical closure of the cervix.

16 Claims, 11 Drawing Figures

CERVICAL CANAL CATHETER

This application is a continuation of application Ser. No. 619,150, filed June 5, 1984, now abandoned.

TECHNICAL FIELD

This invention relates to a cervical canal catheter deviced in order not only to prevent possible complications accompanying premature rupture of membrane before term in a pregnant woman, but also to carry out extraction after positively awaiting the maturity of a fetus.

BACKGROUND ART

The premature rupture of membrane before the beginning of parturition causes an efflux of amniotic fluid from the ruptured part, an onset of labour-pains accompanying the amniorrhea and an ascending intrauterine infection from the ruptured part, and before normal gestation (40 weeks). Thus an immature fetus is born and, both the mother and the fetus are exposed to a serious danger.

Treatment of this disease is roughly divided into (1) positive induction of labor and (2) watchful waiting. The former is based on the assertion that prompt derivery of a fetus followed by care in an incubator is better than exposure to a danger of microbiosis caused sooner or later, and the latter is a method by which extraction is carried out after as sufficient a maturation of a fetus as possible is awaited by intravaginal disinfection and administration of antibiotics and tocolytic agents to the mother body.

However, in the case of the former, the function of lungs (respiratory function) of the fetus is always immature before 35 weeks of gestation, and therefore, there is a risk of respiratory distress syndrome immediately after the birth, so that the life of the fetus is endangered. In the case of the latter, such an effect is found that a stress imposed on the fetus by rupture of membrane accelerates maturation of the function of lungs of the fetus, but the efflux of amniotic fluid cannot but be looked on, and there is always a danger of infection in the amniotic fluid. Recently, in order to prevent infection in amniotic fluid, reports have successively been made on attempts to prevent ascending infection from vagina to uterus by putting a contraceptive pessary on cervix uteri and always injecting thereinto an anticeptic solution. This method permits the prevention to some extent of the ascending infection after the attachment of the pessary, but is ineffective for a case in which an infection in the amniotic fluid has already been caused (usually, bacteria are detected in the amniotic fluid 2 hours after rupture of membrane) and is ineffective for preventing the amniotic fluid from efflux because no close adhesion can be attained between the cervix uteri and the pessary.

Intrauterine environment is an incubator more perfect and comfortable than any other artificial incubator for a fetus which is supplied with nutrients and oxygen by the mother body through placenta as a point of contact. If various complications accompanying the rupture of membrane can be prevented, there will be brought about an epock-making reformation of control of mother and fetus. Under these circumstances, this invention has been accomplished on the basis of the finding that premature rupture of membrane for which no suitable remedy has heretofore been conducted can be kept under positive control by attaching a cervical canal catheter earnestly devised in order to satisfy the above-mentioned clinical requirements, by hysterotrachelorrhaphy (surgical closure of the cervix) which is used for cervical incompetency.

DISCLOSURE OF INVENTION

According to this invention, there is provided a cervical canal catheter, characterized in that a balloon assembly having two lobes, which may be either a gourd-shaped balloon having a narrow part in the middle or two balloons which are independent of each other in the axial direction, are provided around a catheter main tube made of a soft rubber or resin having an open end at the tip of or in the contiguity to the tip of the catheter main tube; that a liquid-medicine-injecting hole is provided in the narrow part of the gourd-shaped balloon or in the valley between the two independent balloons; that a balloon injection-hole and a balloon injection-passage for injecting a gas or a liquid under pressure into each balloon, and a liquid-medicine-injecting passage leading to the liquid-medicine-injecting hole are provided so that a for a majority of the lengths thereof, a side thereof is defined by the wall of the catheter main tube and that at the other end of the catheter main tube, the balloon injection-passage and the liquid-medicine-injecting passage branch off from the catheter main tube.

Figure 1:
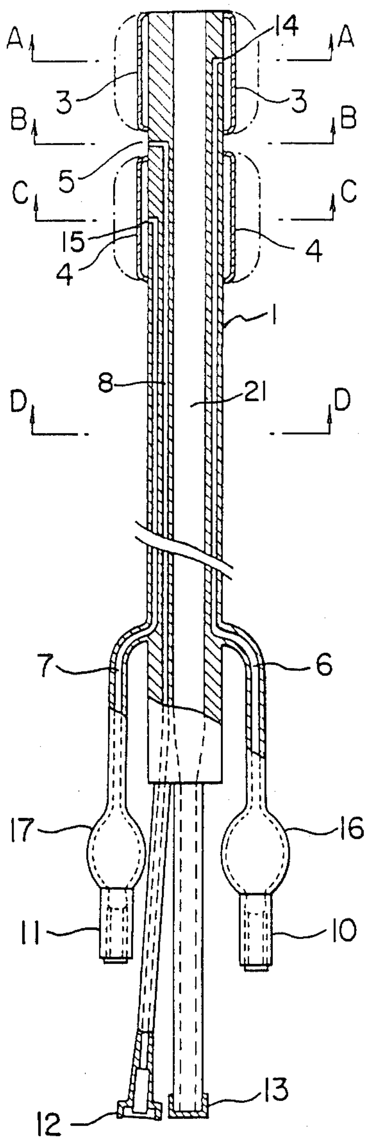
FIG. 1 is a sketch showing a concrete example of this invention.
Figure 2:
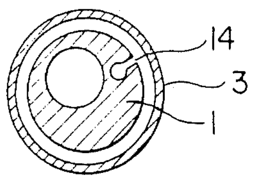
FIGS. 2 to 5 are cross-sectional views along the A—A line, the B—B line, the C—C line and the D—D line, respectively, in FIG. 1.
Figure 3:
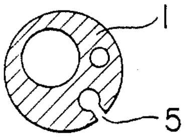
Figure 4:
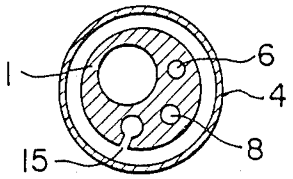
Figure 5:
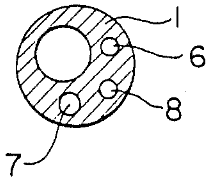

In the drawings, 1 shows a catheter main tube, 2 a gourd-shaped balloon, 3 and 4 balloons, 5 and 5' a liquid-medicine-injecting hole, 6 and 7 balloon injection-passages, 8 a liquid-medicine-injecting passage, 9 a trumpet-shaped film, 10 and 11 check valves, 12 and 13 caps, 14 and 15 balloon injection-holes, 16 and 17 pilot balloons, 18 a uterus, 19 a cervical canal, 20 a ligature thread, and 21 the main cavity of the catheter main tube.

BEST MODE FOR PERFORMING THE INVENTION

Concrete examples of this invention are explained referring to the drawings.

Figure 6:
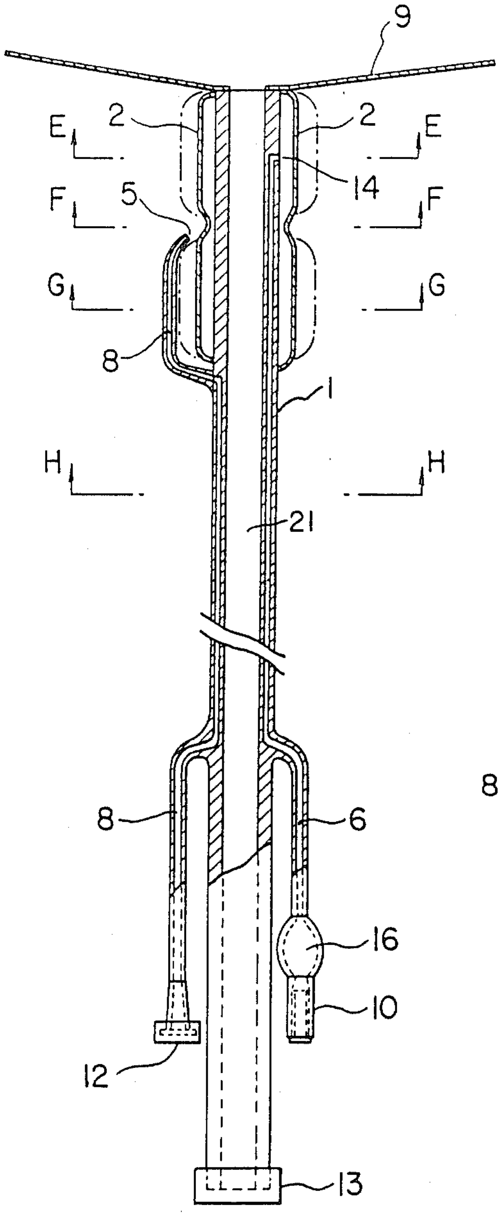
FIG. 6 is a sketch showing another concrete example of this invention.
Figure 7:
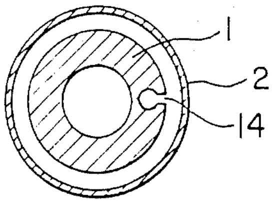
FIGS. 7 to 10 are cross-sectional views along the E—E line, the F—F line, the G—G line and the H—H line, respectively, in FIG. 6.
Figure 8:
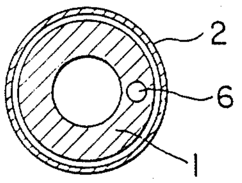
Figure 9:
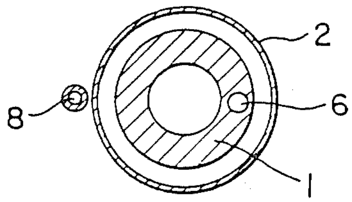
Figure 10:
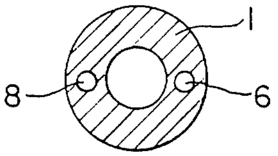

FIG. 1 and FIG. 6 are detailed views of the concrete examples of this invention. This invention is characterized in that a gourd-shaped balloon 2 having a narrow part in the middle or two balloons 3 and 4 which are independent of each other in the axial direction are provided around a catheter main tube 1 made of a soft rubber or resin having an open end at the tip of or in the contiguity to the tip of the catheter main tube; that a liquid-medicine-injecting hole 5 is provided in the narrow part of the gourd-shaped balloon 2 or in the valley between the two independent balloons 3 and 4; that a balloon injection-hole 14 and balloon injection-passages 6 and 7 for injecting a gas or liquid under pressure into the balloons and a liquid-medicine-injecting passage 8 leading to the liquid-medicine-injecting hole 5 are provided in the wall of the catheter main tube 1 or integratedly with the catheter main tube 1; and that at the other end of the catheter main tube, the balloon injection-passages 6 and 7 and the liquid-medicine-injecting passage 8 branch off from the catheter main tube 1. This invention provides a cervical canal catheter comprising them as the basic construction and preferably equipped with a trumpet-shaped film at the open end portion of the catheter main tube 1 in the contiguity to the balloon.

As the soft rubber or resin referred to in this invention, there may be used any of those used generally in the medical instruments, for example, soft vinyl chloride resin, natural rubber, silicone rubber, urethane rubber or the like, and silicone rubber is more suitable than the others because the catheter is allowed to indwell for a long time and the catheter main tube is preferably transparent. The balloon or balloons attached around the catheter main tube in 1 the contiguity to the tip of the catheter main tube 1 may be made of a material which is either the same as or different from the catheter main tube in quality. The shape of the balloon may be the gourd-shaped balloon 2 having a narrow part in the middle as shown in FIG. 6 or may be separated into two balloons 3 and 4 as shown in FIG. 1. What is important is that a narrow valley is formed at the center of the two swellings of the balloon or balloons when the balloon or balloons are expanded, and the liquid-medicine-injecting hole 5 is provided in the valley. As is apparent from the drawings, this narrow section may be no more than about 10% of the length of the balloon assembly. Moreover, it is desirable that the balloon juts out beyond the tip of the catheter main tube 1 upon expansion. The balloon is attached in the contiguity to the tip of the catheter main tube 1, and the length of the whole balloon is preferably 50 mm or less. Each balloon has the balloon injection-hole 14 or 15 on the catheter main tube 1 inside the balloon, and the balloon injection-passages 6 and 7 branch off from the catheter main tube 1 at the other end. To the ends of the injection passages 6 and 7 are preferably attached pilot balloons 16 and 17, respectively, and check valves 10 and 11, respectively. The balloons can be expanded by injecting a gas or liquid under pressure through the respective check valves by means of a syringe, and the turgor condition can be known by means of a pilot balloon. Since the gourd-shaped balloon 2 shown in FIG. 6 is expanded through the single balloon injection-passage 6, the inside pressure of the whole balloon is uniform and the balloon is expanded in the form of a gourd. When the two separate balloons 3 and 4 are used, the respective balloon injection-passages 6 and 7 are independently provided, and therefore, there is such an advantage that the degree of expansion of the two balloons can individually be adjusted.

The liquid-medicine-injecting hole 5 (FIG. 1) or 5' (FIG. 6). to be provided in the valley at the center of the swellings of the balloon or balloons is formed at the end of the liquid-medicine-injecting passage 8 embedded in the wall of the catheter main tube 1 in the concrete example of FIG. 1, but may be formed by leading a fine tube along the outer wall of the balloon as in the case of the gourd-shaped balloon 2 shown in the concrete example of FIG. 6. The other end of the liquid-medicine-injecting passage 8 branches off from the catheter main tube 1, and a cap 12 is attached to the end. It is better to attach a cap 13 to the other end of the catheter main tube 1 in order to prevent any infection during the indwelling. The catheter main tube 1 may be provided with a sampling hole for collecting a humor discharged from the open end at any position along the main cavity 21.

It is preferred that the main cavity 21 of the catheter main tube 1 has such a structure that a fine tube for sampling an amniotic fluid sample can, if necessary, be inserted through the open end.

Figure 11:
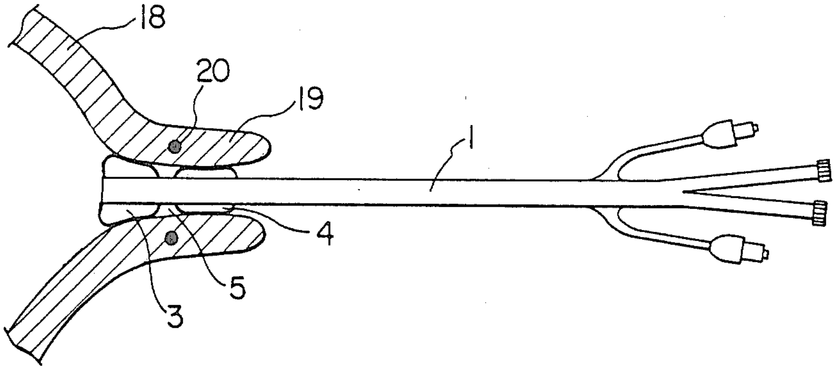
FIG. 11 is an explanatory view showing the condition of use of the cervical canal catheter according to this invention.

In FIG. 11, an explanatory view is given for showing the condition of use of the cervical canal-indwelling catheter according to this invention. The balloons 3 and 4 are used for more intimately adhering the inner surface of a cervical canal subjected to plication and narrowing by surgical ligature to the catheter by means of the turgor of the balloons, and the catheter is allowed to indwell so that the strangulation ring formed by use of a ligature thread coincides in position with the valley between the two balloons 3 and 4. Therefore, an effect of fixing the catheter in the cervical canal is brought about by the ligaturing force and the turgor of the balloons, so that indwelling of the catheter in the cervical canal which has heretofore been unable to imagine has become possible.

The trumpet-shaped film 9 optionally provided in the open end portion of the catheter main tube 1 in the contiguity to the balloon is preferably a flexible orbicular or conical film having a thickness of about 1 mm or less and a diameter of 100 mm or less, and its diameter can be adjusted by cutting the film depending on the degree of opening of the uterus of a patient. the trumpet-shaped film 9 is used for covering a velamentum which has been physically damaged. Since the film is placed along the curve of the interior of uterus it prevents efflux of amniotic fluid from the damaged portions and from ascent of mucus and bacteria from the cervix uteri, and uniformly disperses the rise of the intrauterine pressure by Laplace's theorem to prevent the direction of pressure from being concentrated into the cervix uteri.

As described above, the uterus is physically blocked with the balloons 3 and 4 or the balloon 2 to isolate its inside from the outside, so that it becomes possible to prevent not only the efflux of amniotic fluid but also the infection with bacteria. Further, an antiseptic solution introduced from the liquid-medicine-injecting hole 5 into the valley between the two balloons 3 and 4 or into the narrow part at the center portion of the gourd-shaped balloon 2 shown in the concrete example of FIG. 6 fills up the space between the valley or narrow part and the inner wall of the cervical canal, and therefore, even if bacteria invade from the vagina side, they undergo sterilization in this space. The cervical mucous passes through the space filled with the antiseptic solution and is introduced, together with the antiseptic solution overflow, into the vagina while wetting the inner surface of the cervical canal on the vagina side in relation to the balloon 4 or the gourd-shaped balloon 2.

Since the branch at the other end of the transparent catheter main tube 1 protrudes from the vagina, the properties, in particular, color of the amniotic fluid filling up the catheter can easily be recognized. Therefore, the threatened asphyxia (excretion of meconium) can be diagnosed without using an amnioscope. Further, an amniotic fluid sample indispensable for the manage of a fetus (judgement of the maturation degree of the fetus) can easily be collected at any time from the main cavity 21 of the catheter main tube 1 without need for a conventional transabdominal amniocentesis. It is also possible to collect the amniotic fluid sample by taking off the cap 13 of the catheter main tube 1, inserting another fine tube into the main cavity 21 from the opening at the tip until it reaches the inner part of the uterus, and then collecting the sample through said fine tube.

Even in a case in which a long time has elapsed after the rupture of membrane, the attachment of the catheter according to this invention makes it possible to take off the cap 13 at the other end of the catheter main tube 1 and inject therefrom an antibiotic directly into the amniotic cavity. Therefore, the attachment makes it possible to increase the concentration of the antibiotic in the amniotic fluid certainly as compared with conventional administration through the mother body, and can exhibit effects in the case where infection has already occured (this can be diagnosed from the number of leukocytes in the amniotic fluid and by microscopic examination of bacteria). Further, the attachment enables direct administration of pulmonary maturation promotors (steroid hormones, etc.) or drugs necessary for the management of a fetus to the fetus, and it is expected to establish a way to prenatal treatment which is now the chief desire of perinatal medicine.

As described above, when used together with hysterotrachelorrhaphy, the cervical canal catheter for premature rupture of membrane according to this invention can be expected to bring about the following effects:

(1) In controlling the premature rupture of membrane, efflux of amniotic fluid and concomitant onset of labor pains can be prevented.

(2) The infection in amniotic fluid unavoidable in this disease can be prevented.

(3) The properties of amniotic fluid can visually be observed, and an amniotic fluid sample necessary for the analysis of the amniotic fluid can easily be collected.

(4) Threatened asphyxia or fetal infection can be diagnosed easily and accurately.

(5) Even when infection has already occurred, the chance of subsequent infection is removed, and moreover very effective treatment is made possible by administration of an antibiotic into the amniotic cavity.

(6) Direct administration of fetal pulmonary maturation promotors becomes possible, so that therapeutic effects can be improved.

(7) By co-use of a tocolytic agent, a fetus can be safely managed until it aquires an ability to be adapted to postnatal environment.

(8) Since amniotic fluid can frequently be analyzed, the physiology of fetal growth which has not yet been elucidated can be grasped.

(9) Attachment of the present catheter makes it possible to greatly lighten the rest degree of patients with said disease who have heretofore required absolute rest owing to Trendelenburg position, and the patients can be allowed to walk or even attend a hospital as outpatients depending on cases.

I claim:

1. A cervical canal catheter comprising:

a catheter main tube made of a soft rubber or resin and defining a main cavity therein, said main cavity having an open end at or in contiguity to the tip of said main tube, said tip being essentially perpendicular to a central axis of said main tube;

a balloon assembly, surrounding the outer periphery of the tip, having two expandable lobes of about equal size, a narrow part being present between said two lobes, and being provided around said catheter main tube, said narrow part being adapted for receiving a strangulation ring formed by a ligature, said balloon assembly being of a size and shape adapted for the intimate adhering of said lobes to a cervical canal subjected to plication and narrowing by surgical ligature when said lobes are expanded, thereby fixing said catheter in the cervical canal;

means defining a liquid-medicine injecting hole in the narrow part;

means defining a balloon injection-hole in a part of said catheter main tube surrounded by said balloon assembly for delivering a fluid under pressure into each said lobe to cause said expansion thereof;

a balloon-injection passage for delivering said fluid to said means defining a balloon-injection hole;

a liquid-medicine injecting passage for delivering a liquid medicine to said liquid-medicine injecting hole, an end portion of said liquid medicine injecting passage at said liquid medicine injecting hole extending outside of said balloon assembly;

said balloon injection-passage and said liquid-medicine-injecting passage each having for a majority of the lengths thereof, a side thereof defined by a wall of said catheter main tube, and, at the end of said catheter main tube, branching off from said catheter main tube.

2. A method of obtaining access to the uterus of a female, comprising the steps of:

selecting a cervical canal catheter including:

a catheter main tube made of a soft rubber or resin and defining a main cavity therein, said main cavity having an open end at or in contiguity to the tip of said main tube, said tip being essentially perpendicular to a central axis of said main tube;

a balloon assembly, surrounding the outer periphery of the tip, having two expandable lobes of about equal size, a narrow part being present between said two lobes, and being provided around said catheter main tube, said narrow part being adapted for receiving a strangulation ring formed by a ligature, said balloon assembly being of a size and shape adapted for the intimate adhering of said lobes to a cervical canal subjected to plication and narrowing by surgical ligature when said lobes are expanded, thereby fixing said catheter in the cervical canal;

means defining a liquid-medicine injecting hole in the narrow part;

means defining a balloon injection-hole in a part of said catheter main tube surrounded by said balloon assembly for delivering a fluid under pressure into said each lobe to cause said expansion thereof;

a balloon-injection passage for delivering said fluid to said means defining a balloon-injection hole;

a liquid-medicine injecting passage for delivering a liquid medicine to said liquid-medicine injecting hole;

said balloon injection-passage and said liquid-medicine-injecting passage each having for a majority of the lengths thereof, a side thereof defined by a wall of said catheter main tube, and, at the end of said catheter main tube, branching off from said catheter main tube;

inserting said tip of said catheter into the uterus of said female through said female's cervical canal, with said balloon assembly unexpanded;

securing said narrow part of said catheter to said cervical canal by means of a strangulation ring of ligature thread extending about said narrow part and through walls of said cervical canal; and expanding said balloon assembly.

3. A method according to claim 2 wherein the balloon assembly juts out beyond the tip of the catheter main tube when expanded.

4. A method according to 2, wherein said each lobe of said balloon assembly comprises two independently pressurizable balloons, said means defining a balloon-injection hole comprises two balloon injection holes for independently providing a fluid under pressure to each of said balloons, said balloon injection passage comprises two independent sub-passages for independently providing a fluid under pressure to said balloon injection holes, each of said sub-passages being equipped with a check valve and a pilot balloon, and wherein the end of the catheter main tube and the branched end of the liquid-medicine-injecting passage are individually equipped with a cap.

5. A method according to claim 2 wherein another fine tube can be inserted into the main cavity of the catheter main tube from the other end to the open end.

6. A method according to claim 2, wherein the balloon assembly juts out beyond the tip of the catheter main tube when expanded.

7. A method according to claim 1, wherein said each lobe of said balloon assembly comprises two independently pressurizable balloons, said means defining a balloon-injection hole comprises two balloon injection holes for independently providing a fluid under pressure to each of said balloons, said balloon injection passage comprises two independent sub-passages for independently providing a fluid under pressure to said balloon injection holes, each of said sub-passages being equipped with a check valve and a pilot balloon, and wherein the end of the catheter main tube opposite said tip and the branched end of the liquid-medicine-injecting passage are individually equipped with a cap.

8. A method according to claim 2, wherein another fine tube can be inserted into the main cavity of the catheter main tube from the end of said main tube opposite the open end.

9. The method of claim 2, wherein said narrow part is no more than about 10% of the length of said balloon assembly when said lobes are expanded.

10. The method of claim 2, wherein said balloon assembly is about 50 mm in length when said balloon assembly is expanded.

11. The method of claim 10, wherein said narrow part is no more than about 10% of the length of said balloon assembly when said lobes are expanded.

12. The method of claim 11, wherein said liquid-medicine-injecting passage has a portion thereof, extending at least from said liquid medicine-injecting hole to an end of said balloon assembly closest an end of said main tube opposite said tip, with a cross-sectional area of no more than about one-fourth that of said main cavity.

13. The method of claim 10, wherein said liquid-medicine-injecting passage has a portion thereof, extending at least from said liquid medicine-injecting hole to an end of said balloon assembly closest an end of said main tube opposite said tip, with a cross sectional area of no more than about one-fourth that of said main cavity.

14. The method of claim 1, wherein said liquid-medicine-injecting passage has a portion thereof, extending at least from said liquid medicine-injecting hole to an end of said balloon assembly closest an end of said main tube opposite said tip, with a cross-sectional area of no more than about one-fourth that of said main cavity.

15. The method of claim 2, further comprising injecting an antiseptic solution through said liquid medicine injecting hole into said narrow part after said balloon has been expanded.

16. The method of claim 2, wherein said liquid medicine injecting hole has a cross-sectional area of no more than about one-sixteenth of that of said main cavity.

* * * * *

UNITED STATES PATENT AND TRADEMARK OFFICE
CERTIFICATE OF CORRECTION

PATENT NO. : 4,693,704

DATED : September 15, 1987

INVENTOR(S) : OGITA

It is certified that error appears in the above-identified patent and that said Letters Patent is hereby corrected as shown below:

Claim 7, line 1: Change "1" to read --2--;

Claim 12, line 1: Change "11" to read --2--;

Claim 14, line 1: Change "1" to read --10--.

Signed and Sealed this

Twenty-fifth Day of April, 1989

*Attest:*

DONALD J. QUIGG

*Attesting Officer* *Commissioner of Patents and Trademarks*